United States Patent [19]

Terwilliger

[11] Patent Number: 5,769,795
[45] Date of Patent: Jun. 23, 1998

[54] ECHOGENIC NEEDLE

[76] Inventor: Richard A. Terwilliger, 3321 Rockwood La. South, Estes Park, Colo. 80517

[21] Appl. No.: 601,457

[22] Filed: Feb. 14, 1996

Related U.S. Application Data

[63] Continuation-in-part of Ser. No. 400,368, Mar. 8, 1995, abandoned.

[51] Int. Cl.⁶ ...................................................... A61B 5/00
[52] U.S. Cl. ............................................ 600/567; 600/562
[58] Field of Search ........................... 128/749, 751–754, 128/662.05

[56] References Cited

U.S. PATENT DOCUMENTS

| | | | |
|---|---|---|---|
| 4,401,124 | 8/1983 | Guess et al. | 128/660 |
| 4,977,897 | 12/1990 | Hurwitz | 128/662.05 |
| 5,081,997 | 1/1992 | Bosley, Jr. et al. | 128/662.05 |
| 5,161,542 | 11/1992 | Palestrant | 128/754 |
| 5,201,314 | 4/1993 | Bosley et al. | 128/662.05 |

OTHER PUBLICATIONS

"SonoVu™US–A visible improvement in ultrasound-guided aspiration", E–Z–Em, Inc.; 1990; 1 page.

"SonoVu™US A Multipurpose Ultrasound-Guided Aspiration Needle", Ultrasound Procedures, E–Z–EM, Inc.; 1992, 2 pages.

*Primary Examiner*—Max Hindenburg
*Attorney, Agent, or Firm*—Fleisler, Dubb, Meyer & Lovejoy

[57] ABSTRACT

An echogenic cannula 7 includes a hole provided at the distal tip end 17. Preferably the hole 5 is positioned through a centerline 8 which is spaced from the centerline 6 of the stylet 7 in order to form a concave surface 11 from which sound waves 10 are reflected in order to locate the distal tip end 17.

18 Claims, 6 Drawing Sheets

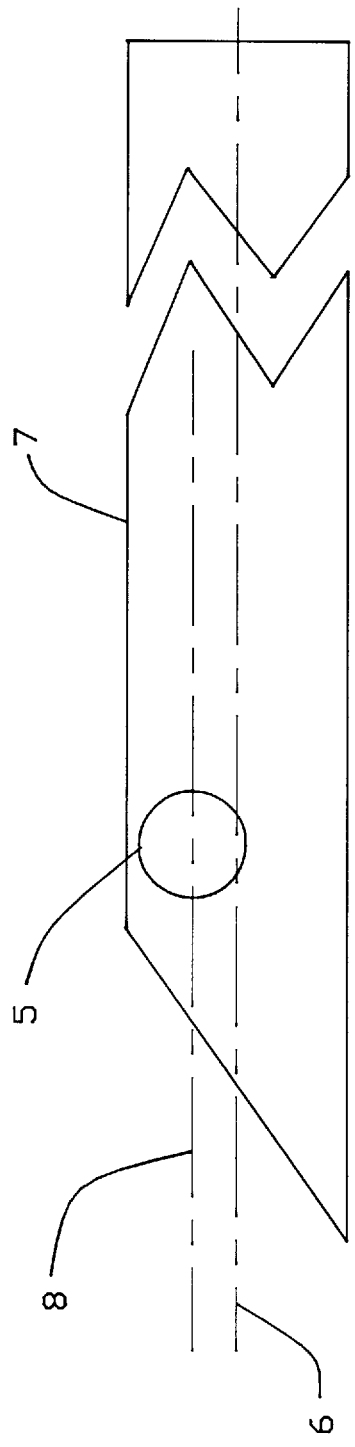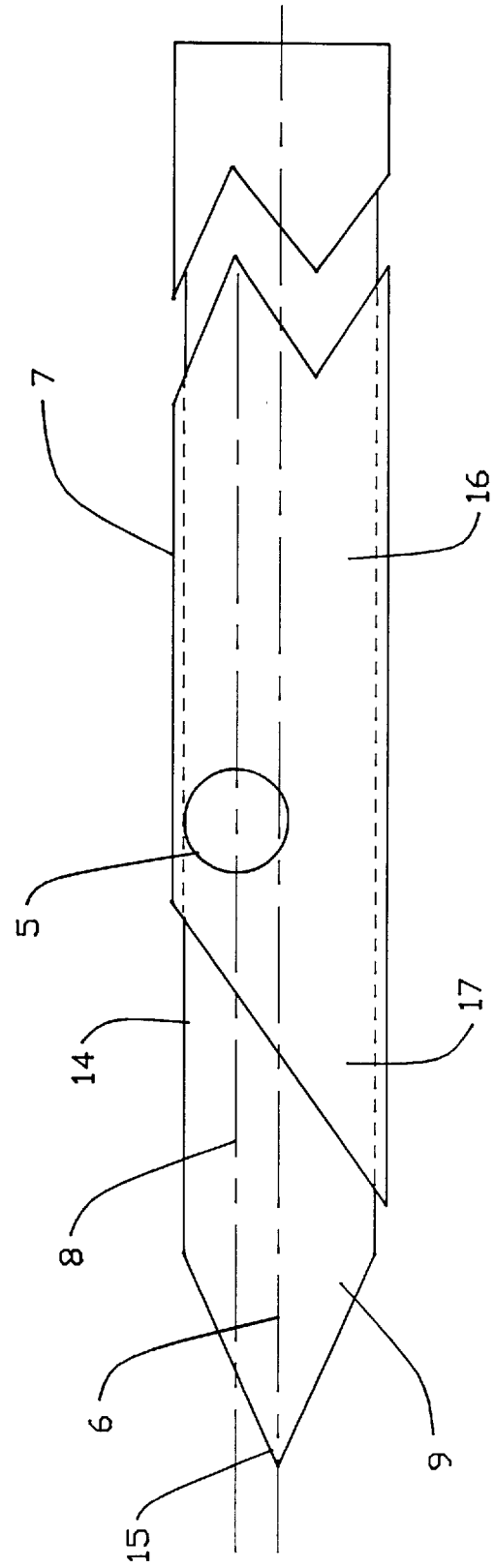

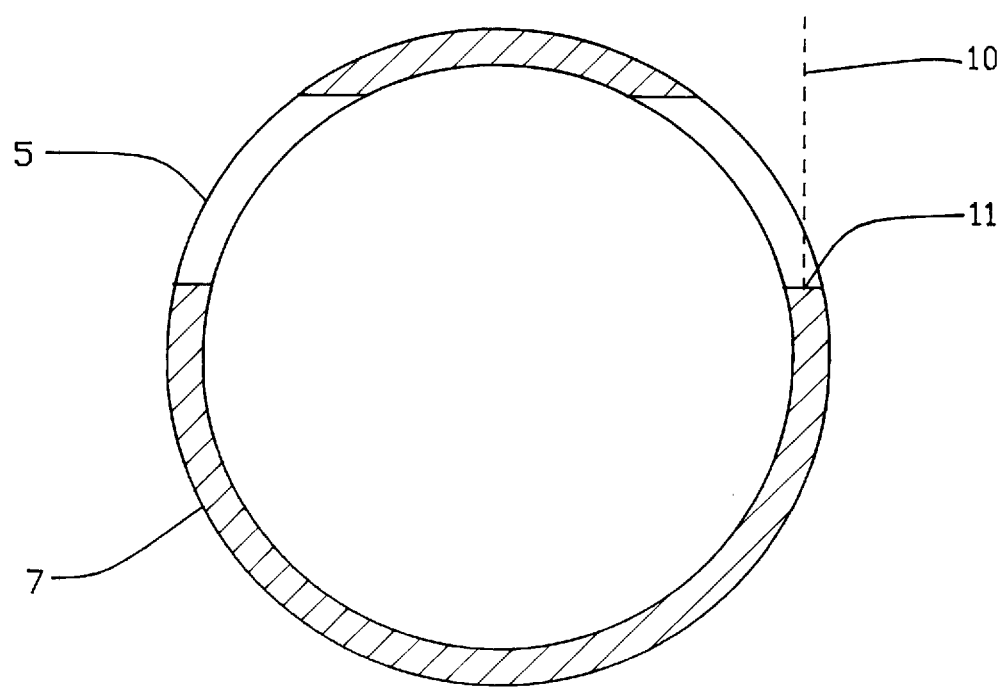
FIG.—5
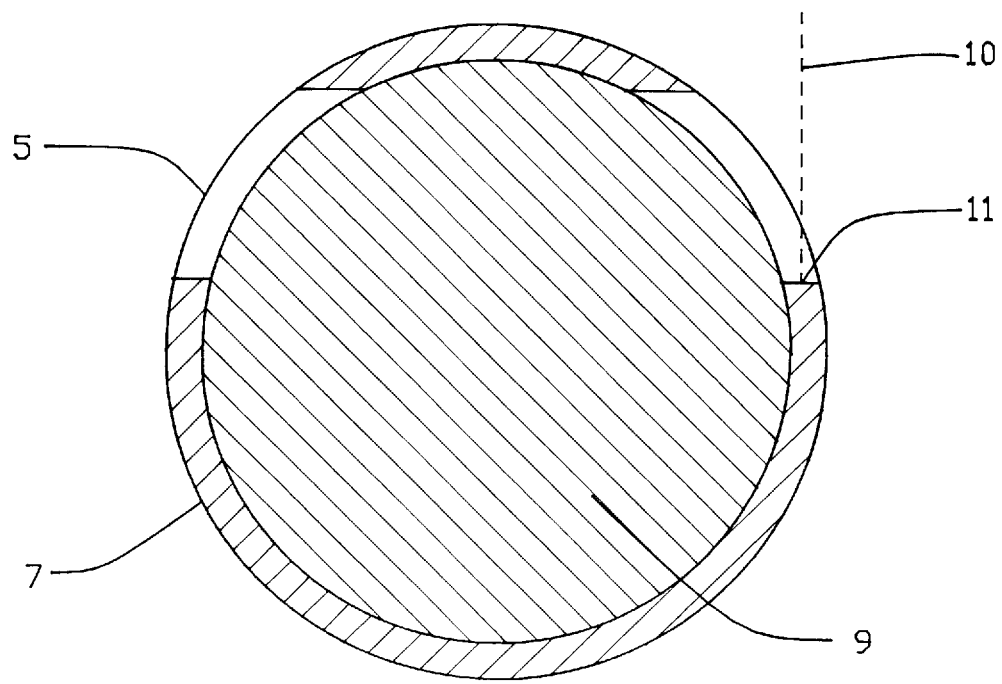
FIG.—6

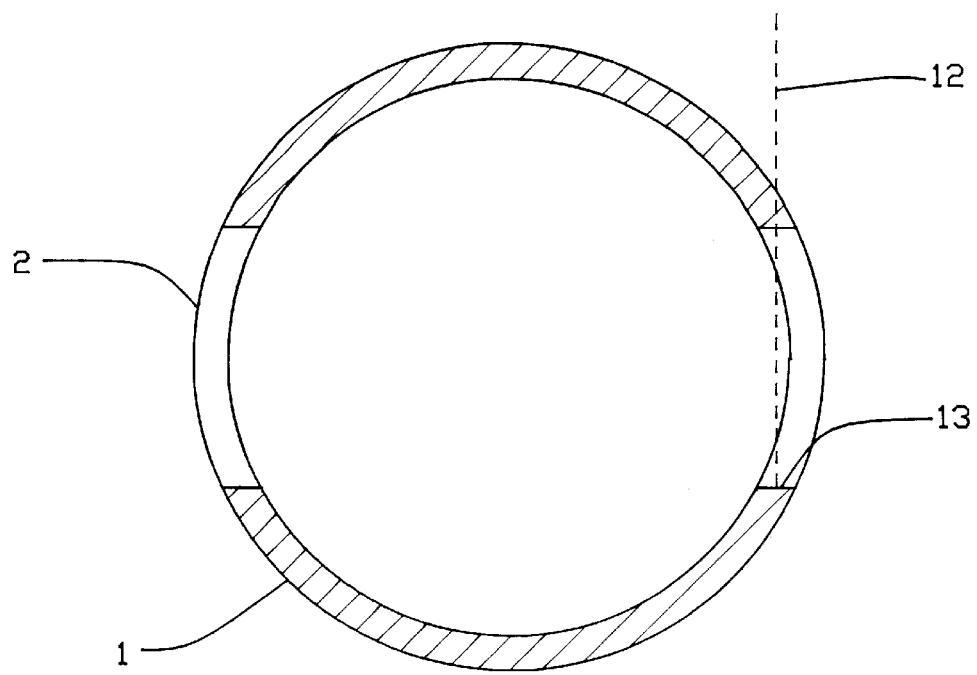
(PRIOR ART)
FIG. —7
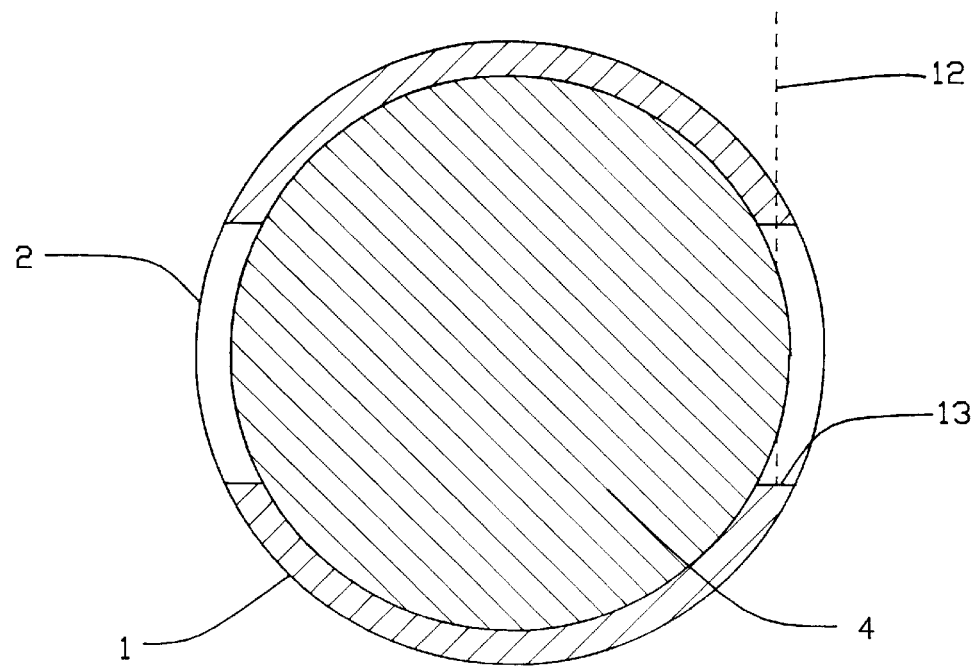
(PRIOR ART)
FIG. —8

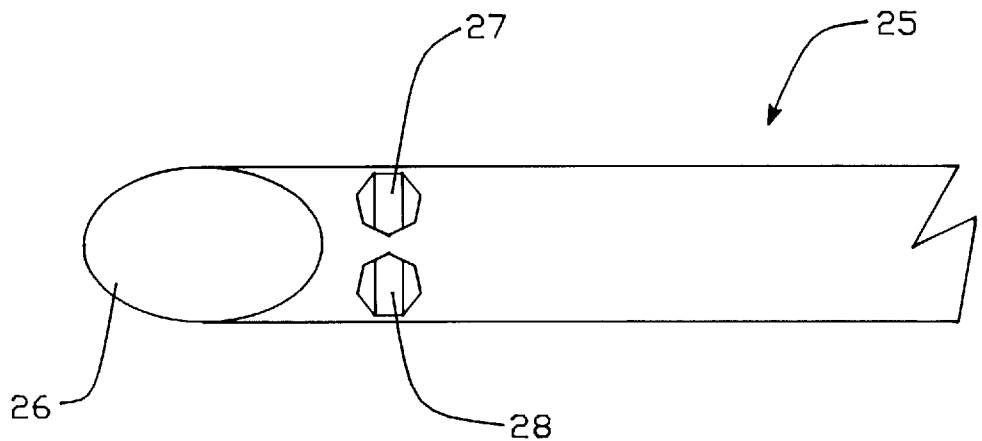
FIG.−11
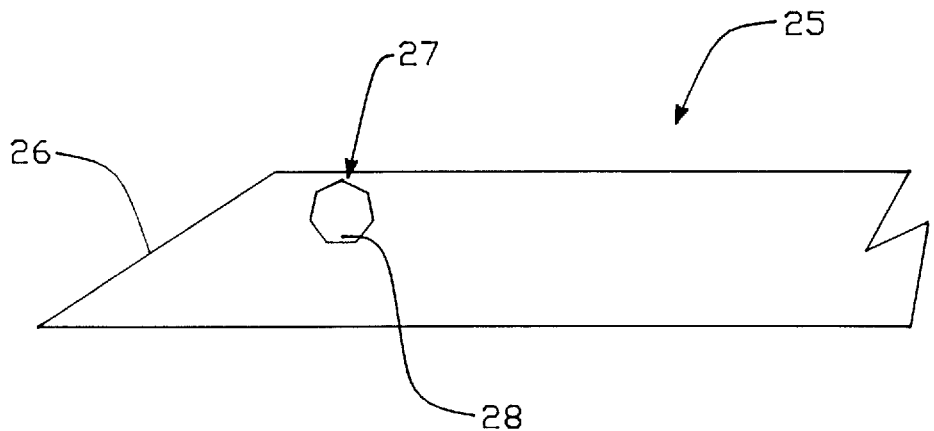
FIG.−12
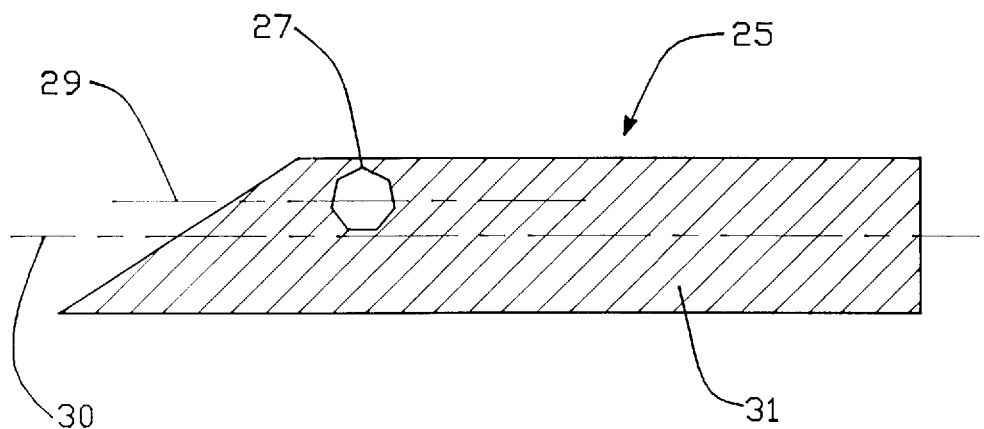
FIG.−13

ECHOGENIC NEEDLE

CROSS REFERENCE

This application is a continuation-in-part of U.S. patent application Ser. No. 08/400,368 filed on Mar. 8, 1995, now abandoned entitled Echogenic Needle Tip and listing Richard A. Terwilliger as the inventor.

FIELD OF THE INVENTION

This invention relates to a new needle tip design to enhance the visibility of, and ability to locate the needle tip during an ultrasound guided needle biopsy procedure. The functionality of this needle tip design is independent of the angle of entry of the needle into the tissue, as it relates to the sound waves generated by the ultrasound transceiver.

This improved needle tip design can be used on the needles of either manual or automated biopsy needle instruments used for the performance of tissue extraction or fluid aspiration visualized under ultrasound guidance.

BACKGROUND OF THE INVENTION

It is often desirable and frequently absolutely necessary to sample or test a portion of tissue from humans and even animals to aid in the diagnosis and treatment of patients with cancerous tumors, premalignant conditions and other diseases or disorders. Typically in the case of cancer or the suspicion of malignant tumors, a very important process call tissue biopsy is performed to establish whether cells are cancerous.

Biopsy may be done by an open or closed technique. Open biopsy removes the entire tissue mass or a part of the tissue mass. Closed biopsy on the other hand is usually performed with a needle-like instrument and may be either an aspiration (hollow needle on a syringe) or a core biopsy (special tissue cutting needle design). In needle aspiration biopsy, individual cells or clusters of cells are obtained for cytologic examination. In core biopsy, a segment of tissue is obtained for histologic examination which may be done as a frozen section or paraffin section.

The methods and procedures of obtaining tissue samples for cytologic or histologic examination have been performed historically by manual insertion and manipulation of the needle. These procedures are performed "blind" by the physician and guided by "feel" and known anatomic "landmarks".

Tumors are first noted in a patient by one of three ways, palpation, x-ray imaging or ultrasound imaging. Once a tumor is identified, a biopsy procedure is performed. Modern medical opinion dictates early detection of cancer increases the likelihood of successful treatment.

The introduction of ultrasound imaging in the field of medical technology has greatly influenced the field of percutaneous tissue biopsy in the last fifteen years. The use of tissue imaging devices that utilize ultrasound waves allows the physician to "see" inside the body and visually guide the needle to the tumor mass. The inherent problem in visualizing the needle is that the angle of entry of the needle into the body in relationship to the direction of the generation of ultrasound waves precludes an optimized reflection of the ultrasound waves back to the transceiver, thus making it extremely difficult to see the needle in the ultrasound image and locate the needle tip in the image in relationship to the anatomic structures of the body.

Attempts in prior art to solve this problem have relied on surface treatments to the outer surface of the hollow needle tube and have been inadequate or only slightly improved visualization at shallow angles of entry of the needle. Examples of such treatments have been described in U.S. Pat. Nos. 4,401,124 (Guess et al.), 5,081,997 (Bosley et al.), and 5,201,314 (Bosley et al.).

These design limitations create a situation of compromise between the steep angle of entry of the needle that is desired in most procedures and the ability of the needle shaft to reflect the ultrasound waves back to the transceiver, thus allowing the needle to be seen in the ultrasound image.

The prior art surface treatments for tissue biopsy needles have been applied to the last part of the distal end of the hollow cannula which is positioned well back from the actual tip of the needle set as it is introduced into the body. This treatment only allows an approximation to be made of the location of the most distal tip of the needle set. The current prior art requires the physician to estimate where the true tip of the needle lies in relation to the internal structures of the tissue.

In order for a surface treatment to be effective at steeper angles of entry, the disrupted surface irregularities must be large enough, in relationship to the length of the sound wave, at the frequencies used to image. If the irregularities are made large enough to properly reflect, the needle shaft is so roughened as to impede the smooth movement of the needle through the tissue and thereby compromising the structure of the tissue to be collected by the needle.

In needles used for aspiration biopsy or for cyst drainage, side port holes have been placed through the diameter of the hollow cannula. It has been claimed that these side ports enhance visualization under ultrasound guidance. Due to the placement of these holes and the nature of how ultrasound waves are reflected, the success of these side ports have had minimal effect on enhancing visualization of the needle under ultrasound guidance.

The requirements to be able to visualize the needle tip at all angles of entry dictate the need for an alternative approach in a design of the needle to allow adequate visualization of the location of the needle during ultrasound imaging. The ideal product would allow the needle to smoothly pass though the tissue and still be visualized at any angle of entry, allowing the physician to obtain the necessary tissue or fluid required to make a diagnosis.

Accordingly it is a principle object of this invention to provide an improved needle design to more reliably visualize the design of the needle under ultrasound guided biopsy procedures.

It is a further object of this invention to provide a needle design that allows the visualization of the needle at any angle of entry into the body in relationship to the generation of sound waves by the ultrasound transceiver.

It is a further object of this invention to provide a needle design that allows visualization that does not impede the smooth passage of the needle through the surrounding tissue.

It is a further object of this invention to provide an improved needle design that allows visualization of the distal tip of the inner stylet or cannula, thus allowing the physician to visualize the extreme distal end of the needle set.

These and other objects of the invention will be apparent from the following descriptions and claims.

SUMMARY OF THE INVENTION

Based on the limitations of prior art instruments for enhancing the visibility of the needle under ultrasound imaging, there exists a need for a needle design which is capable of being visualized at any angle of entry to assist in obtaining biopsy samples with currently available marketed devices.

Accordingly I have invented a needle design that overcomes the limitations of prior art devices.

The needle design can be made an integral part of the inner solid stylet or the cannula of any given needle set which includes a stylet and a cannula. Further, the needle design can be used on either the stylet or the cannula, when the stylet and cannula are not used together in a needle set.

In a preferred form, the stylet or cannula has a hole machined through the distal tip of the diameter of the stylet or cannula, perpendicular to the axis of the stylet or needle. This hole is positioned slightly above the centerline of the stylet or cannula, so the hole breaks out on the diameter as oval openings.

Due to these oval openings, the bottom curved portion of the hole breakouts presents a reflective concave surface that always presents itself as a surface to reflect back the sound wave emitted from the ultrasound transceiver at any relational angle of the needle shaft to the generation of the sound waves.

Since the hole is small in relationship to the diameter of the stylet or cannula, and perpendicular to the axis of the stylet or cannula, the movement of the stylet or cannula through the tissue is not impeded in any significant way.

In alternative embodiments, the hole can have a plurality of shapes from round and smooth to holes created with a multiplicity of sides such as a 9-sided nonagon or other polygon. The multiple sides define the concave surfaces and enhance ultrasound imaging.

BRIEF DESCRIPTION OF THE DRAWINGS

The above noted advantages and other characteristic features of the present invention will be apparent from the accompanying drawings, and in part pointed out in the following detailed description of the preferred embodiment of the invention in which references will be made to the accompanying drawings wherein like reference numerals designate corresponding parts and wherein:

FIGS. 3 and 4 are side views of the preferred embodiment of the inventive needle design.

FIGS. 5 and 6 are cross sectional views of the distal end of the needle at the side port hole illustrating the breakout of the hole through the needle diameter in the preferred embodiment of the inventive needle design.

FIGS. 7 and 8 are cross sectional views of the distal end of the prior art needle at the side port hole illustrating the breakout of the hole through the needle diameter.

FIGS. 10, 12 and 13 are top, side, and cross-sectional views through a stylet of a needle set showing the invented needle design with a polygon-shaped hole provided through the stylet.

DESCRIPTION OF THE PREFERRED EMBODIMENT

Figure 1:
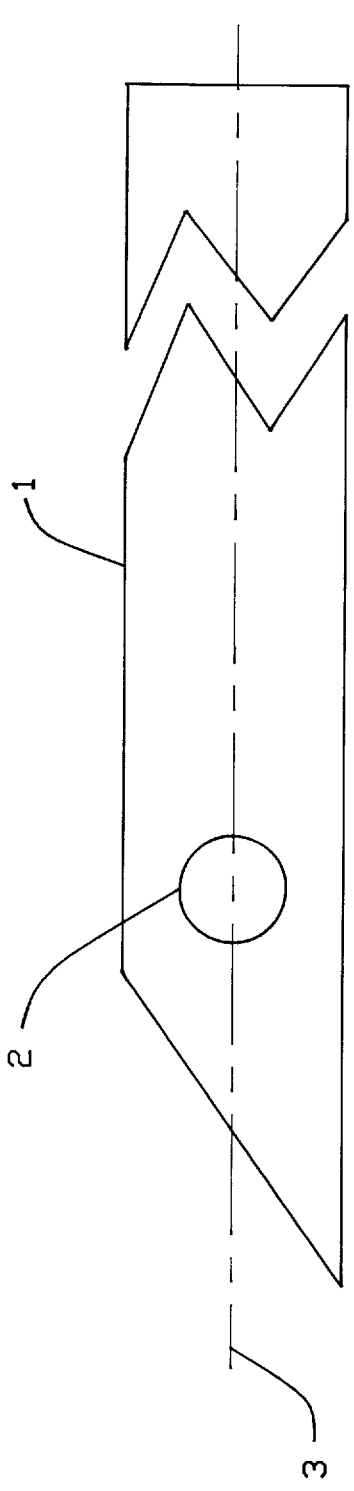
FIGS. 1 and 2 are side views of the distal end of the prior art.

For the purposes of promoting an understanding of the principles of the invention, reference will now be made to the embodiment illustrated in the drawings and specific language will be used to describe the same. It will nevertheless be understood that no limitation of the scope of the invention is thereby intended, and that alterations and further modifications to the illustrated device, and further applications of the principles of the invention as illustrated therein can be contemplated by one skilled in the art to which the invention relates.

Considering now the drawings in detail:

FIG. 1 shows the side view of the distal end of the prior art needle design. Note that in FIG. 1 it shows the hole 2 breaking out on the sides of the cannula diameter on the centerline 3 of the cannula 1.

Figure 2:
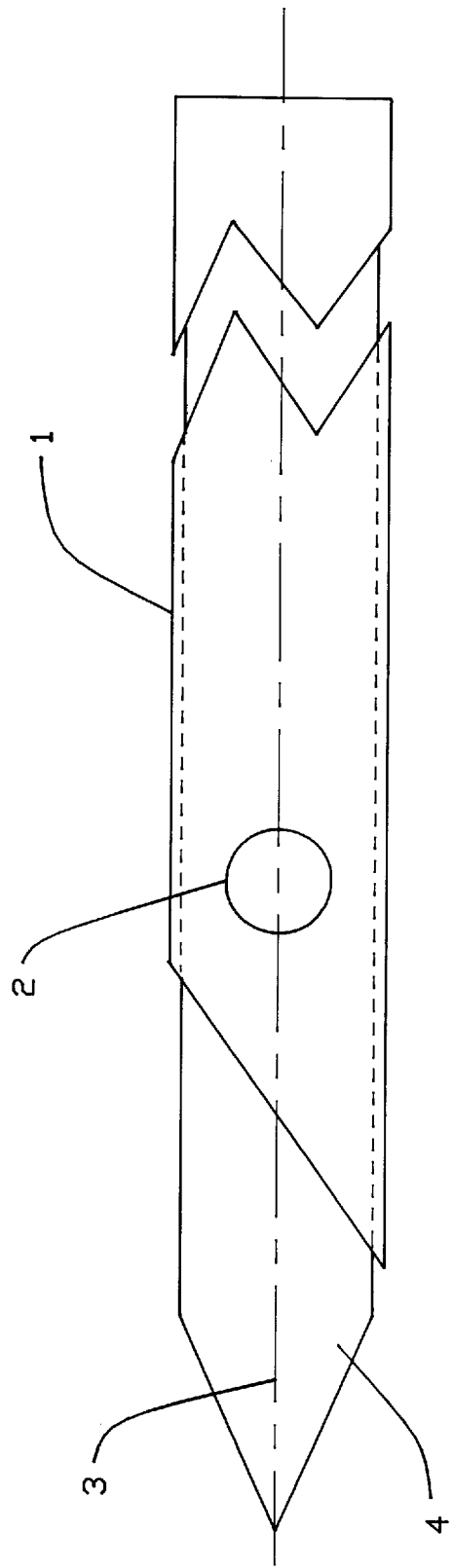

FIG. 2 shows the side view of the distal end of the prior art needle design with a stylet 4 in position. Note that in FIG. 2 it shows the hole 2 breaking out on the sides of the needle diameter on the centerline 3 of the cannula 1.

FIG. 3 shows the side view of the distal end of the preferred embodiment of the inventive needle design. Note that in FIG. 3 it shows the hole 5 breaking out on the sides of the cannula 7 above the centerline 6 of the needle cannula 7 on line 8 which is in this embodiment parallel to centerline 6.

FIG. 4 shows the side view of the distal end of the preferred embodiment of the inventive needle design with a stylet 9 in position in cannula 7. Note that in FIG. 4 it shows the hole 5 breaking out on the sides of the cannula 7 above the centerline 6 of the cannula 7.

In FIG. 4 the stylet 9 includes a needle body 14 with a needle tip 15 at a distal end. The cannula 7 includes a cannula body 16 with a cannula tip 17 at a distal end.

FIG. 5 pictorially illustrates the generated sound waves 10 being able to reflect off the exposed perpendicular concave surface 11 of the hole 5 in the cannula 7. In this embodiment, hole 5 is drilled through cannula 7. However, other techniques can be employed to provide a hole through cannula 7. No structure of the stylet 9 (FIG. 6) with the stylet 9 in place inside the cannula 7, prevents the return echo from reflecting back from the perpendicular concave surface 11 to the transceiver that generated the sound waves. The clear path for the sound waves to the reflective concave surface 11 is created by the hole 5 being positioned above the centerline 6 (FIG. 4) of the cannula 7. This exposed reflective concave surface 11 creates a bright indication in the ultrasound image allowing the visualization of the cannula 7.

FIG. 7 pictorially illustrates in the prior art the generated sound waves 12 attempting to reflect off the exposed perpendicular surface 13 of the hole 2 in the cannula 1. The placement of the hole 2 on the centerline 3 (FIG. 1) of the cannula 1 prevents the return echo from adequately reflecting back from the perpendicular surface 13 to the transceiver that generated the sound waves. In the prior art, a clear path for the sound waves to reach the reflective surface 13 is impeded by the top edge of the hole 2 being positioned on the centerline 3 of the cannula 1. This inability of most of the energy of the sound wave 12 from reaching the exposed reflective surface 13 inhibits the creation of a bright indication in the ultrasound image diminishing the visualization of the cannula 1.

FIG. 8 pictorially illustrates in the prior art the generated sound waves 12 attempting to reflect off the exposed perpendicular surface 13 of the hole 2 in the cannula with the stylet 4 in place. With the stylet in place the placement of the hole 2 on the centerline of the cannula 1 prevents the return echo from reflecting back from the perpendicular surface 13 to the transceiver that generated the sound waves. In the prior art the stylet 4 in position obstructs a clear path for the sound waves to reach the reflective surface 13. This inability of the energy of the sound wave 12 to reach the exposed reflective surface 13 prevents the creation of a bright indication in the ultrasound image diminishing the visualization of the cannula 1.

By way of example only, the present invention can be used in biopsy devices disclosed in the following U.S. patents and U.S. patent applications, all of which are incorporated herein. The U.S. Pat. Nos. include 5,183,052, 5,188,118 and 5,282,476. The U.S. patent applications Ser. Nos. include 08/218,261 and 08/227,660.

Figure 9:
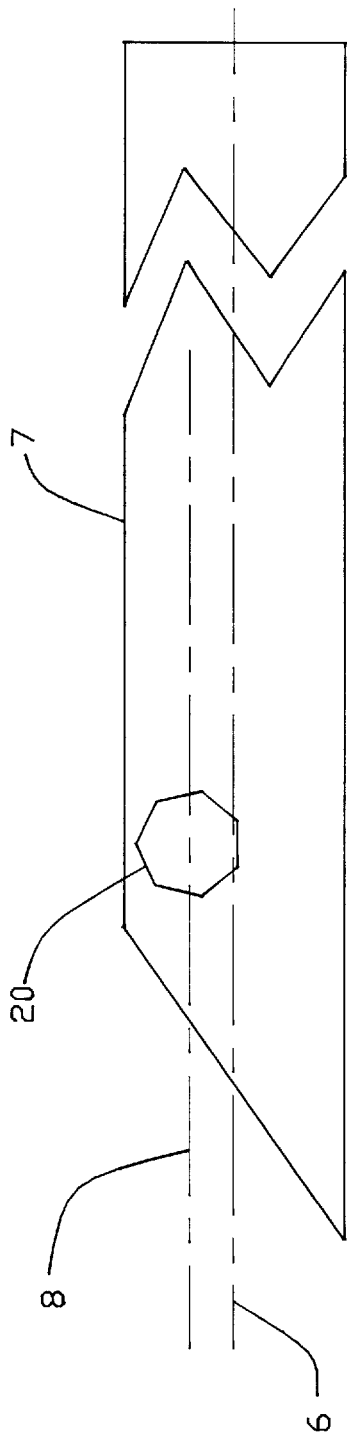
FIGS. 9 and 10 are side views of an alternative preferred embodiment of the invented needle design with the cannula having a polygon-shaped hole provided therethrough.
Figure 10:
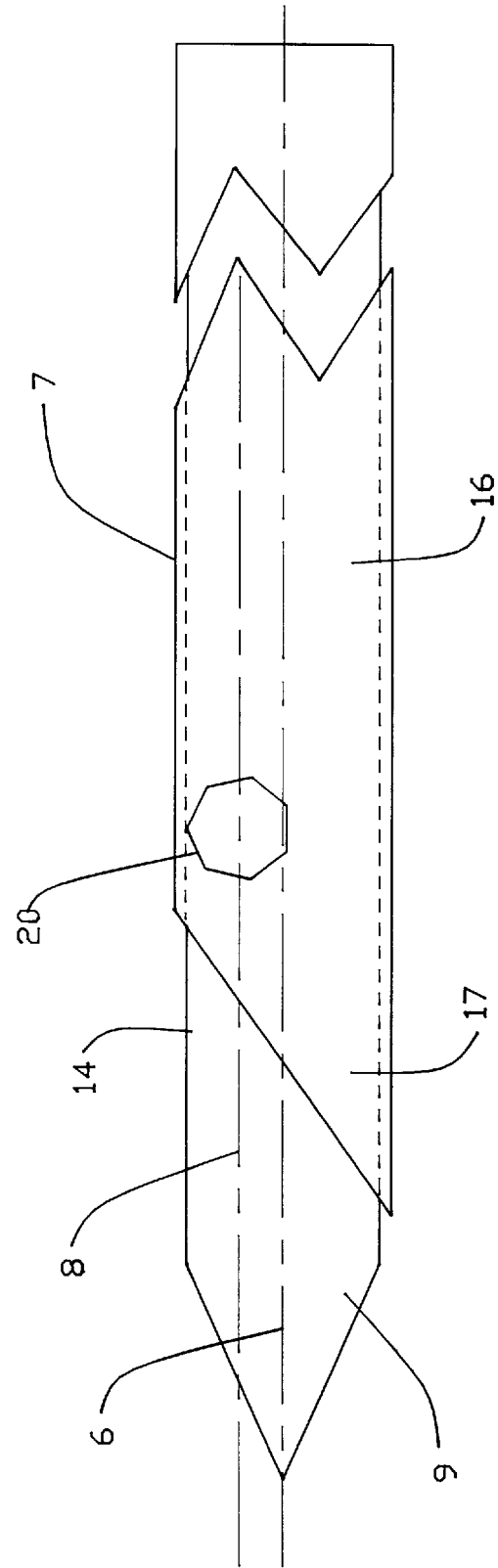

The alternative embodiment of the invention shown in FIGS. 9 and 10 is similar to the invention that is shown in FIGS. 3 and 4 and similar features are identically numbered. In FIG. 9, hole 20 is through a centerline 8 which is spaced from the centerline 6 of the cannula. The hole 20 in this embodiment is a polygon with 7 sides. It is to be understood that in any other polygon-shaped hole such as a 9-sided nonagon, is within the spirit and scope of the invention. With such a multi-sided hole, a concave surface is presented which has multiple angles and corners which are of assistance in reflecting ultrasound images. FIG. 10 depicts a stylet 9 position in the cannula 7.

FIGS. 11, 12 and 13 depict an inventive stylet 25 which can be used in a needle set such as depicted in FIG. 3. The inventive stylet 25 can be positioned inside of a cannula. However, the cannula does not need to have an echogenic hole provided therein. FIGS. 11 and 12 show the top and side views of the distal end of the inventive stylet design. Note that in FIG. 11, the stylet tip 26 shows the side regions of the stylet 25 where the hole 27 breaks out on both of the stylet diameter. The concave bottom surface 28 of the hole 27 presents itself to the generated soundwaves and which soundwaves then bounce back to the transceiver. In this embodiment, the hole 27 is shaped as a polygon having 7 sides. Also preferred would be a 9-sided nonagon. Other polygons and shapes which define a concave surface come within the spirit and scope of the invention.

FIG. 13 illustrates the position of the centerline 29 of the hole 27 in relation to the centerline 30 of the stylet body 31. It is noted that the centerline 29 of the hole 27 is above the centerline 30 of the stylet 31. The centerline 29 may be even more removed from the centerline 30 as long as sufficient concave bottom surface 28 remains for good ultrasound imaging. In this embodiment as shown in FIG. 13, the centerline 29 is substantially parallel to the longitudinal centerline 30. Other aspects of the inventive design can be obtained from a review of the current application, U.S. patent application Ser. No. 08/400,368, filed Mar. 8, 1995, which is incorporated herein.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected. By way of example only, a cannula could be used without a needle in order to locate a surgical site and verify that location with ultrasound imaging. Further, the inventive design could be used on a device other than a cannula and have the present ultrasound imaging advantages.

I claim:

1. A cannula for positioning adjacent to tissue to be biopsed comprising:
    a cannula body with an outer surface and a longitudinal centerline;
    a cannula tip located at a distal end of the cannula body for positioning adjacent to tissue to be biopsed;
    an indentation defined at the cannula tip in order to make the cannula echogenic; and
    said indentation pierces said outer surface of said cannula body and said indentation is directed into said cannula body away from said outer surface, and along an axis that does not intersect the longitudinal centerline, in order not to impede the movement of the cannula through tissue to be biopsed.

2. The cannula of claim 1 wherein:
    said indentation is concave.

3. The cannula of claim 1 wherein:
    said indentation is made by providing a hole at the end of the cannula tip.

4. The cannula of claim 1 wherein:
    said indentation is polygon-shaped.

5. The cannula of claim 1 wherein:
    rearwardly of the indentation the cannula body is smooth in order to provide for smooth passage of the cannula body through tissue.

6. The cannula of claim 3 wherein said hole pierces through the cannula tip at two adjacent locations in order to define exposed adjacent concave surfaces.

7. The cannula of claim 3 wherein said hole pierces through the cannula tip at two adjacent locations in order to define a concave surface which is partially exposed at each of the two adjacent locations.

8. The cannula of claim 1 wherein said indentation provides a reflective surface along a line spaced from the cannula longitudinal centerline.

9. A cannula for positioning adjacent to tissue to be biopsed comprising:
    a cannula body with an outer surface and a longitudinal centerline;
    a cannula tip located at a distal end of the cannula body for positioning adjacent to tissue to be biopsed;
    a hole provided in the cannula body adjacent to the cannula tip in order to make the cannula echogenic; and
    said hole pierces through said outer surface of said cannula body and said hole is directed into said cannula body away from said outer surface, and along an axis that does not intersect the longitudinal centerline, in order not to impede the movement of the cannula through tissue to be biopsed.

10. The cannula of claim 9 wherein:
    said hole defines a concave shape.

11. The cannula of claim 10 wherein:
    said hole is elliptical.

12. The cannula of claim 9 wherein:
    rearwardly of the indentation the cannula body is smooth in order to provide for smooth passage of the cannula body through tissue.

13. The cannula of claim 9 wherein said hole is polygon-shaped.

14. A cannula for positioning adjacent to tissue to be biopsed comprising:
    a cannula body with an outer surface and a longitudinal centerline;
    a cannula tip located at a distal end of the cannula body for positioning adjacent to tissue to be biopsed;
    an echogenic mark defined at the cannula tip in order to make the cannula tip echogenic; and
    said echogenic mark pierces through said outer surface of said cannula body and said echogenic mark is directed into said cannula body away from said outer surface, and along an axis that does not intersect the longitudinal centerline, in order not to impede the movement of the cannula through tissue to be biopsed.

15. The cannula of claim 14 wherein said echogenic mark is polygon-shaped.

16. A needle set comprising:

a cannula having a cannula body with an outer surface and a longitudinal centerline;

a cannula tip located at a distal end of the cannula body for positioning adjacent to tissue to be biopsed;

an echogenic mark defined at the cannula tip in order to make the cannula tip echogenic;

a stylet having a stylet body;

the cannula having an inner bore which receives the stylet body;

said stylet positioned in the cannula body preparatory to the needle set addressing tissue to be biopsed with the stylet tip positioned just past the tip of the cannula such that the cannula presents a smooth surface for penetrating the tissue while the echogenic mark allows the tip of the cannula to be tracked; and said echogenic mark pierces through said outer surface of said cannula body and said echogenic mark is directed into said cannula body away from said outer surface, and along an axis that does not intersect the longitudinal centerline, in order not to impede the movement of the cannula through tissue to be biopsed.

17. A stylet that can be positioned adjacent to tissue to be biopsed comprising:

a stylet body with an outer surface;

a stylet tip located at a distal end of the stylet body adapted to be positioned adjacent to tissues to be biopsed;

said stylet body has a longitudinal centerline;

said hole is provided in the stylet body in order to make the stylet echogenic;

said hole is in the shape of a polygon; and said hole pierces through said outer surface of said stylet body and said hole is directed into said stylet body away from said outer surface, and along an axis that does not intersect the longitudinal centerline, in order not to impede the movement of the cannula through tissue to be biopsed.

18. A stylet that can be positioned adjacent to tissues to be biopsed, the stylet comprising:

a stylet body with an outer surface and a longitudinal centerline;

a stylet tip located at a distal end of the stylet body adapted to be positioned adjacent to tissues to be biopsed;

an indentation defined at the stylet tip in order to make the stylet echogenic;

said indentation being in the shape of a polygon; and said indentation pierces through said outer surface of said stylet body and said indentation is directed into said stylet body away from said outer surface, and along an axis that does not intersect the longitudinal centerline, in order not to impede the movement of the cannula through tissue to be biopsed.

* * * * *